US007698156B2

(12) United States Patent
Martucci et al.

(10) Patent No.: US 7,698,156 B2
(45) Date of Patent: Apr. 13, 2010

(54) SYSTEM AND METHOD FOR IDENTIFYING DATA STREAMS ASSOCIATED WITH MEDICAL EQUIPMENT

(75) Inventors: James P. Martucci, Libertyville, IL (US); William R. Richardson, Etobicoke (CA)

(73) Assignee: Baxter International Inc., Deerfield, IL (US)

( * ) Notice: Subject to any disclaimer, the term of this patent is extended or adjusted under 35 U.S.C. 154(b) by 1974 days.

(21) Appl. No.: 10/424,553

(22) Filed: Apr. 28, 2003

(65) Prior Publication Data

US 2004/0019464 A1 Jan. 29, 2004

Related U.S. Application Data

(63) Continuation-in-part of application No. 10/135,180, filed on Apr. 30, 2002, which is a continuation-in-part of application No. 10/059,929, filed on Jan. 29, 2002.

(51) Int. Cl.
G06Q 10/00 (2006.01)
G06Q 50/00 (2006.01)
G06F 19/00 (2006.01)
A61B 5/00 (2006.01)

(52) U.S. Cl. .................................... 705/3; 705/2; 705/4
(58) Field of Classification Search .................... 705/2, 705/3, 4
See application file for complete search history.

(56) References Cited

U.S. PATENT DOCUMENTS 4,857,716 A * 8/1989 Gombrich et al. ........... 235/375

| 5,401,059 A | 3/1995 | Ferrario |
| 5,406,473 A | 4/1995 | Yoshikura et al. |
| 5,416,695 A | 5/1995 | Stutman et al. |
| 5,417,222 A | 5/1995 | Dempsey et al. |

(Continued)

FOREIGN PATENT DOCUMENTS

CA 1293566 12/1991

(Continued)

OTHER PUBLICATIONS

Daniel J. Nigrin and Isaac S. Kohane, "*Glucoweb: A Case Study of Secure, Remote Biomonitoring and Communication,*" Proceedings of the 2000 AMIA Annual Symposium, 2000, 5 pages, American Medical Informatics Association, Bethesda, MD.

(Continued)

*Primary Examiner*—Gerald J. O'Connor
*Assistant Examiner*—Amber L Altschul
(74) *Attorney, Agent, or Firm*—K&L Gates LLP

(57) ABSTRACT

A system and method for uniquely identifying data streams associated with medical equipment are described. The system may be implemented in a variety of ways, including as a combination of a medical device, a data stream identifier, and a medical device identifier. The medical device generates a plurality of data streams. The data streams are uninterrupted transmissions of data from the medical device. The data streams include information regarding the operation of the medical device. The data stream identifier attaches a unique data tag to the data streams. The medical device identifier is configured to generate a medical device tag. The medical device tag includes information to uniquely identify the medical device and is accessible from an external computer. The data stream identifier and the medical device identifier are secured to the medical device.

52 Claims, 5 Drawing Sheets

U.S. PATENT DOCUMENTS

| | | | |
|---|---|---|---|
| 5,420,977 A | 5/1995 | Sztipanovits et al. | |
| 5,421,343 A | 6/1995 | Feng | |
| 5,429,602 A | 7/1995 | Hauser | |
| 5,433,736 A | 7/1995 | Nilsson | |
| 5,438,607 A | 8/1995 | Przygoda, Jr. et al. | |
| 5,441,047 A | 8/1995 | David et al. | |
| 5,445,621 A | 8/1995 | Poli et al. | |
| 5,458,123 A | 10/1995 | Unger | |
| 5,467,773 A | 11/1995 | Bergelson et al. | |
| 5,468,110 A | 11/1995 | McDonald et al. | |
| 5,485,408 A | 1/1996 | Blomquist | |
| 5,502,944 A | 4/1996 | Kraft et al. | |
| 5,507,412 A | 4/1996 | Ebert et al. | |
| 5,526,428 A | 6/1996 | Arnold | |
| 5,528,503 A | 6/1996 | Moore et al. | |
| 5,531,697 A | 7/1996 | Olsen et al. | |
| 5,531,698 A | 7/1996 | Olsen | |
| 5,536,084 A | 7/1996 | Curtis et al. | |
| 5,537,313 A | 7/1996 | Pirelli | |
| 5,542,420 A | 8/1996 | Goldman et al. | |
| 5,544,649 A | 8/1996 | David et al. | |
| 5,544,661 A | 8/1996 | Davis et al. | |
| 5,547,470 A | 8/1996 | Johnson et al. | |
| 5,553,609 A | 9/1996 | Chen et al. | |
| 5,558,638 A | 9/1996 | Evers et al. | |
| 5,558,640 A | 9/1996 | Pfeiler et al. | |
| 5,560,352 A | 10/1996 | Heim et al. | |
| 5,562,232 A | 10/1996 | Pearson | |
| 5,562,621 A | 10/1996 | Claude et al. | |
| 5,564,803 A | 10/1996 | McDonald et al. | |
| 5,569,186 A | 10/1996 | Lord et al. | |
| 5,569,187 A | 10/1996 | Kaiser | |
| 5,573,506 A | 11/1996 | Vasko | |
| 5,579,001 A | 11/1996 | Dempsey et al. | |
| 5,579,378 A | 11/1996 | Arlinghaus, Jr. | |
| 5,581,687 A | 12/1996 | Lyle et al. | |
| 5,582,593 A | 12/1996 | Hultman | |
| 5,590,648 A | 1/1997 | Mitchell et al. | |
| 5,594,786 A | 1/1997 | Chaco et al. | |
| 5,597,995 A | 1/1997 | Williams et al. | |
| 5,598,536 A | 1/1997 | Slaughter, III et al. | |
| 5,613,115 A | 3/1997 | Gihl et al. | |
| 5,619,991 A | 4/1997 | Sloane | |
| 5,626,144 A | 5/1997 | Tacklind et al. | |
| 5,630,710 A | 5/1997 | Tune et al. | |
| 5,637,082 A | 6/1997 | Pages et al. | |
| 5,640,953 A * | 6/1997 | Bishop et al. | 600/300 |
| 5,643,212 A | 7/1997 | Coutre et al. | |
| 5,647,854 A | 7/1997 | Olsen et al. | |
| 5,651,775 A | 7/1997 | Walker et al. | |
| 5,658,250 A | 8/1997 | Blomquist et al. | |
| 5,664,270 A | 9/1997 | Bell et al. | |
| 5,666,404 A | 9/1997 | Ciccotelli et al. | |
| 5,681,285 A | 10/1997 | Ford et al. | |
| 5,683,367 A | 11/1997 | Jordan et al. | |
| 5,687,717 A | 11/1997 | Halpern et al. | |
| 5,687,734 A | 11/1997 | Dempsey et al. | |
| 5,697,951 A | 12/1997 | Harpstead et al. | |
| 5,699,350 A | 12/1997 | Kraslavsky | |
| 5,700,998 A | 12/1997 | Palti | |
| 5,704,351 A | 1/1998 | Mortara et al. | |
| 5,704,364 A | 1/1998 | Saltzstein et al. | |
| 5,712,912 A | 1/1998 | Tomko et al. | |
| 5,713,485 A | 2/1998 | Liff et al. | |
| 5,713,856 A | 2/1998 | Eggers et al. | |
| 5,715,823 A | 2/1998 | Wood et al. | |
| 5,724,025 A | 3/1998 | Tavori | |
| 5,732,709 A | 3/1998 | Tacklind et al. | |
| 5,734,831 A | 3/1998 | Sanders | |
| 5,735,887 A | 4/1998 | Barreras, Sr. et al. | |
| 5,737,539 A | 4/1998 | Edelson et al. | |
| 5,752,976 A | 5/1998 | Duffin et al. | |
| 5,769,811 A | 6/1998 | Stacey et al. | |
| 5,772,586 A | 6/1998 | Heinonen et al. | |
| 5,772,637 A | 6/1998 | Heinzmann et al. | |
| 5,776,057 A | 7/1998 | Swenson et al. | |
| 5,781,442 A | 7/1998 | Engleson et al. | |
| 5,782,878 A | 7/1998 | Morgan et al. | |
| 5,785,650 A | 7/1998 | Akasaka et al. | |
| 5,788,669 A | 8/1998 | Peterson | |
| 5,790,409 A | 8/1998 | Fedor et al. | |
| 5,795,327 A | 8/1998 | Wilson et al. | |
| 5,803,906 A | 9/1998 | Pratt et al. | |
| 5,805,442 A | 9/1998 | Crater et al. | |
| 5,807,336 A | 9/1998 | Russo et al. | |
| 5,810,747 A | 9/1998 | Brudny et al. | |
| 5,813,972 A | 9/1998 | Nazarian et al. | |
| 5,822,544 A | 10/1998 | Chaco et al. | |
| 5,832,448 A | 11/1998 | Brown | |
| 5,833,599 A | 11/1998 | Schrier et al. | |
| 5,836,910 A | 11/1998 | Duffy et al. | |
| 5,841,975 A | 11/1998 | Layne et al. | |
| 5,842,976 A | 12/1998 | Williamson | |
| 5,848,593 A | 12/1998 | McGrady et al. | |
| 5,855,550 A | 1/1999 | Lai et al. | |
| 5,857,967 A | 1/1999 | Frid et al. | |
| 5,935,099 A * | 8/1999 | Peterson et al. | 604/65 |
| 5,959,529 A * | 9/1999 | Kail, IV | 340/539.12 |
| 5,960,085 A * | 9/1999 | de la Huerga | 340/5.61 |
| 6,231,560 B1 * | 5/2001 | Bui et al. | 604/500 |
| 2001/0048027 A1 * | 12/2001 | Walsh | 235/385 |

FOREIGN PATENT DOCUMENTS

| | | |
|---|---|---|
| CA | 2370758 A1 | 10/2001 |
| EP | 0 505 627 A2 | 9/1992 |
| EP | 0 595 474 A2 | 5/1994 |
| EP | 0 814 393 A1 | 12/1997 |
| EP | 0 844 581 A2 | 5/1998 |
| EP | 0 838 768 A3 | 1/1999 |
| EP | 0 958 778 A1 | 11/1999 |
| GB | 2 285 135 A | 6/1995 |
| JP | 61066950 A | 4/1986 |
| JP | 10-149270 | 6/1998 |
| JP | 10-254806 | 9/1998 |
| WO | WO 84/00493 A2 | 2/1984 |
| WO | WO 91/04759 A1 | 4/1991 |
| WO | WO 93/02720 A1 | 2/1993 |
| WO | WO 94/05355 A1 | 3/1994 |
| WO | WO 94/08647 A1 | 4/1994 |
| WO | WO 94/12235 A1 | 6/1994 |
| WO | WO 94/24929 A1 | 11/1994 |
| WO | WO 95/02426 A1 | 1/1995 |
| WO | WO 95/23378 A2 | 8/1995 |
| WO | WO 95/32480 A1 | 11/1995 |
| WO | WO 96/16685 A1 | 6/1996 |
| WO | WO 96/25877 A2 | 8/1996 |
| WO | WO 96/36923 A1 | 11/1996 |
| WO | WO 97/18636 A2 | 5/1997 |
| WO | WO 98/26365 A1 | 6/1998 |
| WO | WO 98/28676 A2 | 7/1998 |
| WO | WO 98/29790 A2 | 7/1998 |
| WO | WO 98/53581 A1 | 11/1998 |
| WO | WO 98/59487 A1 | 12/1998 |
| WO | WO 99/10029 A1 | 3/1999 |
| WO | WO 99/10830 A1 | 3/1999 |
| WO | WO 99/13400 A1 | 3/1999 |
| WO | WO 00/13588 A1 | 3/2000 |
| WO | WO 00/43941 A1 | 7/2000 |
| WO | WO 00/60522 A2 | 10/2000 |
| WO | WO 00/60522 A3 | 10/2000 |
| WO | WO 00/69331 A1 | 11/2000 |
| WO | WO 00/79466 A2 | 12/2000 |
| WO | WO 01/01305 A1 | 1/2001 |

| WO | WO 01/01321 A1 | 1/2001 |
| WO | WO 01/65463 A2 | 9/2001 |
| WO | WO 01/88828 A2 | 11/2001 |
| WO | WO 02/06793 A1 | 1/2002 |
| WO | WO 02/33961 A1 | 4/2002 |

OTHER PUBLICATIONS

Stephen S. Wang and Justin Starren, "*A Web-Based, Secure, Light Weight Clinical Mulitmedia Data Capture and Display System*," 5 pages, Proceedings of the 2000 AMIA Annual Symposium, 2000, 5 pages, American Medical Informatics Association, Bethesda, MD.

Web site information, Information Data Management, Inc.'s PCMS: Plasma Center Management System, Dec. 14, 2001, 11 pages.

Laura Landro, "*Electronic Medical Records Call for Common Language by Doctors*," taken from the Wall Street Journal, Aug. 15, 2002, p. D4.

Product literature, Baxter Healthcare Corporation, "MultiPlex™ Series 100 Fluid Management System," undated, 2 pages.

Web site Information, Wyndgate Technologies' SafeTrace Tx™, undated, 15 pages.

Clayton M. Curtis, "*A Computer-based Patient Record Emerging from the Public Sector: The Decentralized Hospital Computer Program*," First Annual Nicholas E. Davies Award Proceedings of the CPR Recognition Symposium, 1995, pp. 75-132, Computer-based Patient Record Institute, Inc, Bethesda, MD.

Larry B. Grandia, B.S.E., et al., "*Building a Computer-based Patient Record System in an Evolving Integrated Health System*," First Annual Nicholas E. Davies Award Proceedings of the CPR Recognition Symposium, 1995, pp. 19-55, Computer-based Patient Record Institute, Inc, Bethesda, MD.

Suzanne Carter, RN, Ed. D., Ann C. Sullivan, MBA, and Margaret Broderick, MBA, MPA, "*The Computer-based Patient Record: The Jacobi Medical Center Experience*," Second Annual Nicholas E. Davies Award Proceedings of the CPR Recognition Symposium, 1996, pp. 71-95, Computer-based Patient Record Institute, Inc, Bethesda, MD.

James Kazmer, Katie Oliver, and Alexander Crosby, "The Creation of a Virtual Medical Record," 1996, 17 pages.

*Standard Specification for Transferring Clinical Observations Between Independent Computer Systems*, Aug. 10, 1997; 79 pages, ASTM E 1238-97, West Conshohocken, PA, United States.

*Standard Specification for Transferring Information Between Clinical Instruments and Computer Systems*, Dec. 10, 1997; 15 pages, ASTM E 1394-97, West Conshohocken, PA, United States.

T.E. Bozeman, et al., "*The Development and Implementation of a Computer-Based Patient Record in a Rural Integrated Health System*," Third Annual Nicholas E. Davies Award Proceedings of the CPR Recognition Symposium, 1997, pp. 101-130, Computer-based Patient Record Institute, Inc, Bethesda, MD.

Clement J. McDonald, M.D., et al., "*The Three-Legged Stool: Regenstrief Institute for Health Care*," Third Annual Nicholas E. Davies Award Proceedings of the CPR Recognition Symposium, 1997, pp. 131-158, Computer-based Patient Record Institute, Inc, Bethesda, MD.

*Standard Guide for Description of Reservation/Registration-Admission, Discharge, Transfer (R-ADT) Systems for Electronic Health Record (EHR) Systems*, Nov. 10, 2000; 7 pages, ASTM E 1239-00, West Conshohocken, PA, United States.

Product literature, Abbott Laboratories' LIFECARE® Blue Line System, Jul. 1990, 15 pages.

*Specification for Low-Level Protocol to Transfer Messages Between Clinical Laboratory Instruments and Computer Systems*, Mar. 11, 1991; 7 pages, ASTM E 1381-91, Philadelphia, PA, United States.

"*BLOCK Medical: Growing With Home Infusion Therapy*," taken from Invivo, The Business and Medicine Report, Apr. 1991; pp. 7-9.

*Standard Specification for Transferring Clinical Observations Between Independent Computer Systems*, Nov. 14, 1991; 64 pages, ASTM E 1238-91, Philadelphia, PA, United States.

Gilad J. Kuperman, M.D., Bette B. Maack, R.R.A., Kay Bauer, R.R.A., and Reed M. Gardner, Ph.D., "*Innovations and research review: The impact of the HELPS computer on the LDS Hospital paper medical record*," Topics in Health Record Management, 1991, pp. 76-85, vol. 12, Issue 2, Aspen Publishers, Inc.

Bell Atlantic Healthcare Systems, Inc., court exhibit, *StatLan Functions and Features*, Specification, release 3.5, dated Nov. 12, 1992. 49 pages.

Allan T. Pryor, "*Current State of Computer-based Patient Record Systems*," Aspects of the Computer-based Patient Record, 1992, pp. 67-82, Springer-Verlag, New York, NY.

Clement J. McDonald, M.D., et al., "*The Regenstrief Medical Record System: 20 Years of Experience in Hospitals, Clinics, and Neighborhood Health Centers*," M.D. Computing, 1992, pp. 206-217, vol. 9, No. 4, Springer-Verlag, New York, NY.

"*The Longitudinal Clinical Record: A View of the Patient*," taken from Proceedings of the 1994 Annual HIMSS Conference, Feb. 14, 1994, pp. 239-250, Healthcare Information and Management Systems Society, Chicago, Illinois, USA.

*Standard Specification for Low-Level Protocol to Transfer Messages Between Clinical Laboratory Instruments and Computer Systems*, Oct. 10, 1995; 7 pages, ASTM E1381-95, West Conshohocken, PA, United States.

Jane B. Metzger and Jonathan M. Teich, "*Designing Acceptable Patient-Care Information Systems*," 1995, pp. 83-132, Springer-Verlag, New York, New York, U.S.A.

A.H. McMorris, J.L. Kelleway, B. Tapadia and E.L. Dohmann, "*Are Process Control Rooms Obsolete?*", taken from Control Engineering, pp. 42-47, Jul. 1971.

J.C. Crone, Jaromir Belic and Roger W. Jelliffee, M.D., "*A Programmable Infusion Pump Controller*," taken from 30 Annual Conference on Engineering in Medicine and Biology, Nov. 5-9, 1977; pp. A-35826 through A-35837.

T. Allan Pryor, Homer R. Warner, and Reed M. Gardner, "*Help—A Total Hospital Information System*," Proceedings of the Fourth Annual Symposium on Computer Applications in Medical Care, Nov. 2-5, 1980, pp. 3-7, vol. 1, Institute for Electrical and Electronics Engineers, New York, NY.

Karen E. Bradshaw, et al., "*Physician decision-making—Evaluation of data used in a computerized ICU*," International Journal of Clinical Monitoring and Computing, 1984, pp. 81-91, vol. 1, Martinus Nijhoff Publishers, Netherlands.

L.C. Sheppard, "*Computer Based Clinical Systems: Automation and Integration*," taken from 39th ACEMB, Sep. 13-16, 1986; pp. 73-75.

Peter Lord, et al., "*MiniMed Technologies Programmable Implantable Infusion System*," Annals New York Academy of Sciences, pp. 66-71, describing clinical trials from Nov. 1986.

Howard L. Bleich, et al., "*Clinical Computing in a Teaching Hospital*," Use and Impact of Computers in Clinical Medicine, 1987, pp. 205-223 and selected pages, Springer-Verlag, New York, NY.

*Standard Guide for Description of Reservation/Registration-Admission, Discharge, Transfer (R-ADT) Systems for Automated Patient Care Information Systems*, May 12, 1988, 10 pages, ASTM E 1239-88, Philadelphia, PA, United States.

Product literature, Baxter Healthcare Corporation, "MultiPlex™ Series 100 Fluid Management System," 1988, 2 pages.

Product literature, Health Data Sciences' ULTICARE™, 1989, 15 pages.

PCT/US03/13095 Nov. 21, 2008 Written Opinion.

* cited by examiner

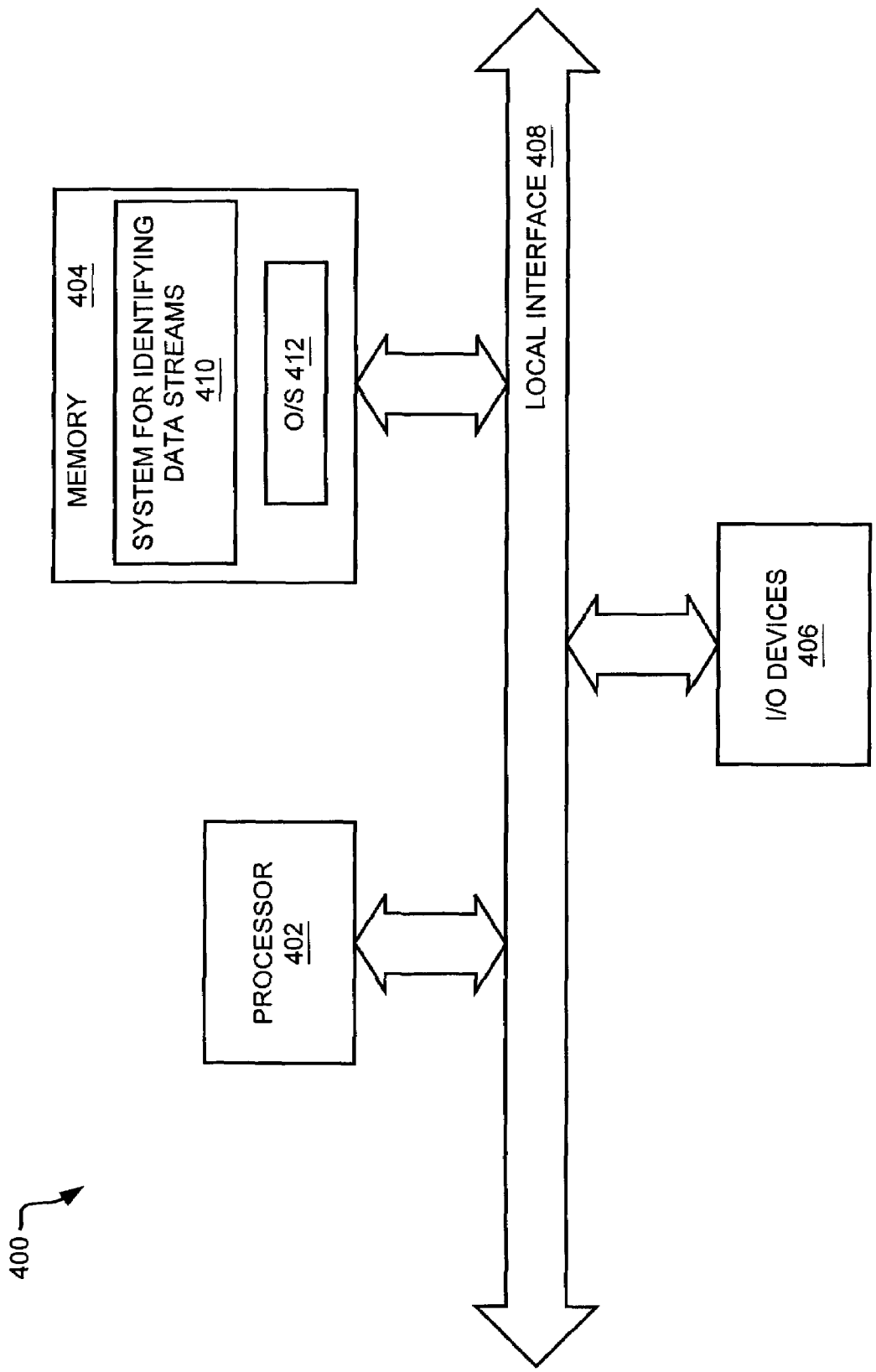

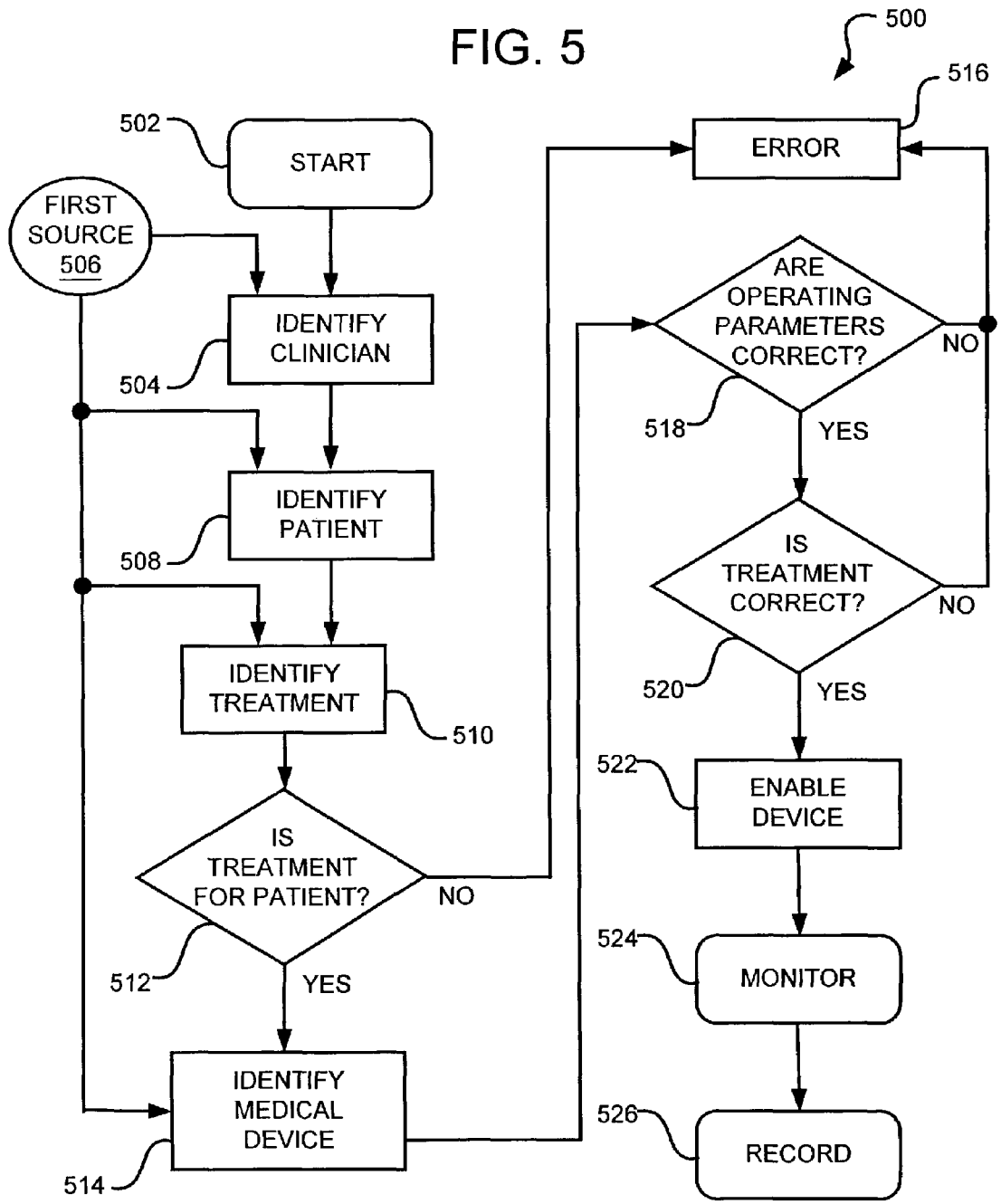

SYSTEM AND METHOD FOR IDENTIFYING DATA STREAMS ASSOCIATED WITH MEDICAL EQUIPMENT

CROSS-REFERENCE TO RELATED APPLICATIONS

This application is a continuation-in-part of copending U.S. utility applications entitled: "Medical Treatment Verification System and Method," having Ser. No. 10/135,180 and filed Apr. 30, 2002 which is incorporated herein by reference; and "System and Method for Operating Medical Devices," having Ser. No. 10/059,929 and filed Jan. 29, 2002 which is incorporated herein by reference. Application Ser. No. 10/135,180 is a continuation-in-part of U.S. utility application Ser. No. 10/059,929.

TECHNICAL FIELD

This invention relates generally to a system and method for operating medical devices and communication with such devices. The invention relates to a system and method for verifying that the right medication is provided to the right patient in the right dose at the right time, and via the right route. More particularly, the invention relates to a system and method for uniquely identifying data streams associated with medical equipment.

BACKGROUND OF THE INVENTION

Patient care systems typically include computer networks, medical devices for treating a patient, and controls for the medical devices. Although patient care systems have been improved through the use of computerized automation systems and methods, patient care systems continue to rely heavily upon manual data management processes for medical devices and controls for medical devices. For example, nursing stations are typically connected to the computer networks in modern hospitals, but it is unusual for the computer network to extend to a patient's room. Computer networks offer the opportunity for automated data management processing including the operating and monitoring of medical devices and controls for the medical devices at the point-of-care. Despite advances in the field, automated data management technology has been underutilized for point-of-care applications due to a lack of more efficient systems and methods for operating medical devices such as infusion pumps.

One of the great hazards in the medical field is the possibility of errors in medication delivery systems due to human error. Computer networks have the potential to minimize the hazards of errors in medication delivery due to human error. Computer networks have the potential for relating medical equipment and patients in order to minimize the possibility of medication errors. Medication errors may be caused by misidentification of medical devices and the lack of or misidentification of data streams associated with computerized medical devices. In order to minimize the possibility of medication errors, the industry is in need of more efficient systems and methods for uniquely identifying data streams associated with medical equipment.

SUMMARY OF THE INVENTION

The present invention provides a system and method for uniquely identifying data streams associated with medical equipment. The system can be implemented in a variety of ways, including as a combination of a medical device, a data stream identifier, and a medical device identifier. The medical device generates a plurality of data streams. The data streams are uninterrupted transmissions of data from the medical device. The data streams include information regarding the operation of the medical device. The data stream identifier attaches a unique data tag to the data streams. The medical device identifier is configured to generate a medical device tag. The medical device tag includes information to uniquely identify the medical device and is accessible from an external computer. The data stream identifier and the medical device identifier are secured to the medical device.

When implemented as a method, the invention can be implemented in a variety of ways, including as a combination of the following steps: generating a plurality of data streams with a medical device, generating a unique data tag using a data stream identifier; attaching the unique data tag to the data streams; and generating a medical device tag upon request from an external computer. The data streams are uninterrupted transmissions of data from the medical device and include information regarding the operation of the medical device. A medical device identifier is accessible from an external computer and generates the medical device tag to uniquely identify the medical device. The data stream identifier and the medical device identifier are secured to the medical device.

Other systems, methods, features, and advantages of the present invention will be, or will become, apparent to one having ordinary skill in the art upon examination of the following drawings and detailed description. It is intended that all such additional systems, methods, features, and advantages included within this description, be within the scope of the present invention, and be protected by the accompanying claims.

BRIEF DESCRIPTION OF THE DRAWINGS

The invention can be better understood with reference to the following drawings. The components in the drawings are not necessarily to scale, emphasis instead being placed upon clearly illustrating the principles of the present invention. In the drawings, like reference numerals designate corresponding parts throughout the several views.

FIG. 4 is a block diagram of a computer system representative of the pharmacy computer, the central system, and/or the digital assistant of FIG. 1. The computer system can include portions of the system for uniquely identifying data streams associated with medical equipment. The computer system can be used in the method and system of uniquely identifying data streams associated with medical equipment; and, FIG. 5 is a flowchart showing an exemplar embodiment of the method for uniquely identifying data streams associated with medical equipment that can be practiced as a computer program in the computer system of FIG. 4.

DETAILED DESCRIPTION

Figure 1:
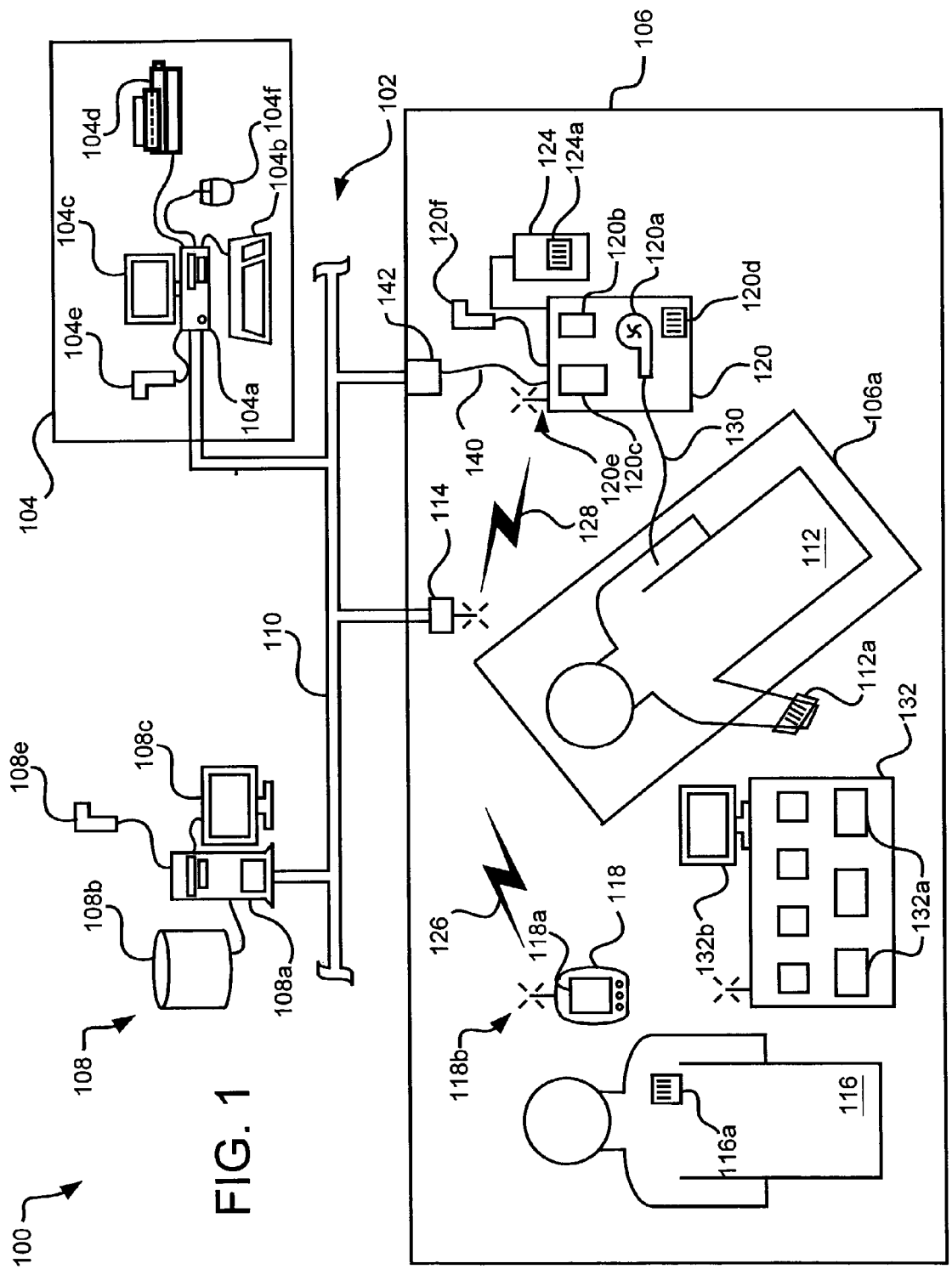
FIG. 1 is a graphical representation of a patient care system. The patient care system includes a pharmacy computer and a central computer system. The patient care system also includes a digital assistant and a medical device at a treatment location.

FIG. 1 is a graphical representation of an embodiment of a patient care system 100. In the embodiment, the patient care system 100 includes a pharmacy computer 104, a central computer system 108, and a treatment location 106. Medical equipment at the treatment location 106 includes a digital assistant 118, a medical treatment cart 132, and an infusion pump 120. The patient care system 100, the central computer system 108, and the treatment location 106 are linked by a network 102. In an embodiment, the pharmacy computer 104 can include a processing unit 104a, a keyboard 104b, a video display 104c, a printer 104d, a bar code reader 104e, and a mouse 104f. Although not shown in FIG. 1, the patient care system 100 can also include subsystems for hospital administration, nursing stations, a clinical information subsystem, a hospital information subsystem, an Admissions Discharge and Transfer (ADT) subsystem, a billing subsystem, and/or other subsystems typically included in patient care systems.

In an embodiment, the central system 108 includes a central servicing unit 108a, a database 108b, a video display 108c, a bar code reader 108e, other input/output components, and many other components known to those having ordinary skill in the art. The network 102 can include a cable communication system 110 portion and a wireless communication system portion. The cable communication system 110 can be, but is not limited to, an Ethernet cabling system, and a thin net system.

In an embodiment, the treatment location 106 includes the medical equipment and a treatment bed 106a. In FIG. 1, a clinician 116 and a patient 112 are shown in the treatment location 106. Medication 124 can be of a type administered to the patient 112 by using the infusion pump 120. Medication 124 can also be of a type administered without using an infusion pump. Infusion pump 120 can be, but is not limited to, the type that administers medication from an infusion bag or the type that administers medication through a syringe. Medication 124 can be stored in medication storage areas 132a of medical treatment cart 132. The clinician 116 uses a hand-held computer, such as digital assistant 118, while administering medication 124 to the patient 112.

In the course of treating patient 112, the clinician 116 can use the digital assistant 118 to communicate with the other portions of the system 100 via cable communication system 110 and a first wireless communication path 126. The infusion pump 120 can have the ability to communicate with the system 100 via cable communication system 110 and second wireless communication path 128 through methods such as, but not limited to Bluetooth and Wifi technologies. Medical treatment cart 132 can also have the ability to communicate via a wireless communication path (not shown in FIG. 1). A wireless transceiver 114 interfaces between the wireless communication devices and cable communication system 110. The wireless communication system portion of the network can employ technology such as, but not limited to, those known to persons having ordinary skill in the art such as IEEE 802.11a, IEEE 802.11b "Wireless Ethernet" through 802.11g, Bluetooth, a local area network, wireless local area networks, a network having a tree topography, a network having a ring topography, wireless internet point of presence systems, an Ethernet, the Internet, radio communications, infrared, fiber optic, and telephone. Though shown in FIG. 1 as a wireless communication system, any of the communication paths shown can also be hardwired communication paths, if desired.

Figure 2:
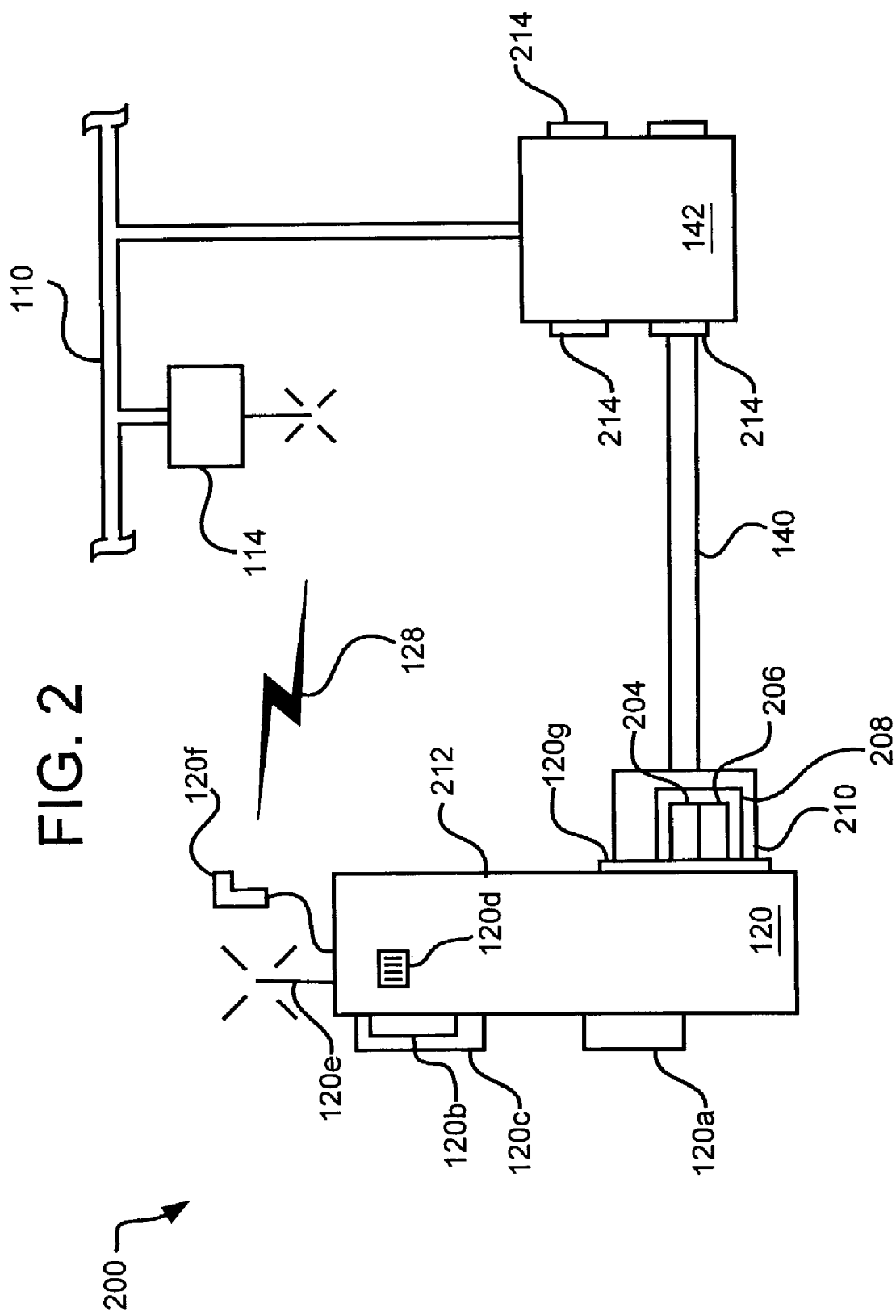
FIG. 2 is a block diagram of the medical device of FIG. 1.

In an embodiment, infusion pump 120 can also have the ability to communicate with the cable communication system 110 via cable communication path 140. Bridge 142 provides an interface between cable communication path 140 and cable communication system 110. Though, shown in FIG. 1 as communicating with a single infusion pump 120, the system described herein for identifying data streams associated with medical equipment allows for the bridge 142 to communicate with a plurality of infusion pumps through a plurality of ports 214 (FIG. 2).

In the patient care system 100, a physician (not shown) can order medication 124 for patient 112. Alternatively, the order can also originate with a clinician 116 at the treatment location 106. The physician and/or clinician 116 can use a computerized physician order entry system (CPOE) and/or the medical treatment cart 132 to order the medication 124 for the patient 112. Those having ordinary skill in the art are familiar with basic CPOE systems. Despite its name, any clinician 116 can use the CPOE. If the medication 124 is one that is efficient to administer through infusion pump 120, the order includes information for generating operating parameters for the infusion pump 120. The operating parameters are the information and/or instruction set that is necessary to program a medical device, such as an infusion pump 120, to operate in accordance with the order.

The order can be entered in the pharmacy computer 104 via input/output devices such as the keyboard 104b, the mouse 104f, a touch screen display, the CPOE system and/or the medical treatment cart 132. Those having ordinary skill in the art are familiar with these and similar input/output devices. The processing unit 104a is able to transform a manually entered order into computer readable data. Devices such as the computerized prescribing order entry system can transform an order into computer readable data prior to introduction to the processing unit 104a. The operating parameters can then be printed in a bar code format by the printer 104d on a medication label 124a. The medication label 124a can then be affixed to a medication 124 container. The medication 124 container is then transported to the treatment location 106. The medication 124 can then be administered to the patient 112 in a variety of ways known in the art including orally and through an infusion pump 120. If the medication 124 is administered orally, the clinician 116 can communicate via the digital assistant 118 and/or the medical treatment cart 132. Medical treatment cart 132 is computerized and generally has a keyboard (not shown), a display 132b, and other input/output devices such as a bar code scanner (not shown). It is also possible, if desired, to enter the order at the treatment location 106 using the digital assistant 118, medical treatment cart 132, and/or input devices associated with the infusion pump 120.

As indicated previously, at the treatment location the medication 124 can be mounted on the infusion pump 120 wherein an intravenous (IV) line 130 is run from the infusion pump 120 to the patient 112. The infusion pump 120 can include a pumping unit 120a, a keypad 120b, a display 120c, an infusion pump ID 120d, an antenna 120e (for Bluetooth, Wifi, or other tadio technology transmission and/or reception) and a bar code reader 120f. The barcode reader 120f can be incorporated into the infusion pump 120 housing or may be connected via a communication cable. Infusion pumps not originally equipped with wireless capability can be provided with a wireless adaptor (not shown) for assisting in the identification of data streams. The wireless adaptor can use a short-range radio technology such as Bluetooth, a long-range radio technology such as Wifi, or other radio technology. Moreover, the wireless adaptor can have its own battery if necessary to avoid reducing the battery life of the host infusion pump, or the wireless adaptor can operate from power supplied by the infusion pump. In an embodiment, the wireless adaptor can also use intelligent data management such as, but not limited to, store and forward data management and data compression to minimize power consumption. The wireless adaptor can also include the ability to communicate with the digital assistant 118 even when the network 102 is not functioning.

The patient care system 100 can include a variety of identifiers such as, but not limited to, personnel, equipment, and medication identifiers. As shown in FIG. 1, the clinician 116 has a clinician badge 116a identifier, the patient 112 has a wristband 112a identifier, the medical device has an equipment identifier (For example, the infusion pump 120 can have an infusion pump ID 120d identifier), and the medication 124 has a medication label 124a identifier. Clinician badge 116a, wristband 112a, infusion pump ID 120d, and medication label 124a include information to identify the personnel, equipment, and medication they are associated with. If desired, the identifiers can also have additional information. For example, the medication label 124a can include information regarding the intended recipient of the medication 124, operating parameters for infusion pump 120, and information regarding the lot number and expiration of medication 124. The information included in the identifiers can be printed, but is preferably in a device readable format such as, but not limited to, an optical readable device format such as a bar code, a radio frequency (RF) device readable format such as an RFID, an iButton, a smart card, and a laser readable format. The digital assistant 118 can include a display 118a and can have the ability to read the identifiers including biometric information such as a fingerprint.

The wristband 112a is preferably attached to the patient 112 as the patient 112 enters a medical care facility. As stated previously, the wristband 112a includes a patient identifier. The patient identifier can include printed information to identify the patient and additional information such as a treating physician's name(s). The patient identifier for patient 112 can include information such as, but not limited to, the patient's name, age, social security number, the patient's blood type, address, allergies, a hospital ID number, and the name of a patient's relative.

FIG. 2 is a block diagram 200 of the medical device of FIG. 1. Consistent with FIG. 1, the medical device is depicted as an infusion pump 120. The components of infusion pump 120 are analogous to many other medical device components known to those having ordinary skill in the art. While infusion pump 120 is used to describe the system and method for uniquely identifying data streams associated with medical device and equipment, the invention can be employed with any medical devices or equipment that communicates via network 102 (FIG. 1). FIG. 2 includes a data stream identifier 204 and a medical device identifier 206 secured to infusion pump 120. Although not necessary, the data stream identifier 204 and the medical device identifier 206 can be packaged in the same housing 208 and they can be electrically interconnected in order to efficiently complete their respective tasks. The housing 208 can be incorporated into a connector 210, such as but not limited to, a DB 9 connector, or similar connectors known to those having ordinary skill in the art. In other embodiments, the data stream identifier 204 and the medical device identifier 206 can be packed inside of the infusion pump housing 212.

Infusion pump 120 can include an equipment ID, such as infusion pump ID 120d, and a bar code reader 120f and a communication port 120g. Infusion pump ID 120d can be a bar code label. The communication port 120g can be a conventional communication port, such as but not limited to, a serial communication port, a RS232, a RS485, and other communication ports known to those having ordinary skill in the art.

Infusion pump 120 provides data to network 102 (FIG. 1). The data is in the form of data packets. The data packets are also known as data streams. As used herein, "data packets" and "data streams" both refer to a preferably uninterrupted, but not necessarily, package of data as recognized by the network. In other words, the terms refer to a package of data that the network 102 recognizes as coming from a single originating point and in a grouping that the network 102 processes as a discrete grouping of data from the medical device. The system for identifying data identifies the data streams originating from a medical device such that the network can identify all data from the medical device as originating from the medical device. Therefore, the exact size and characteristics of the data stream are dependent upon the characteristics of the medical device and the network. Regardless of the exact size and characteristics of the data stream, the data stream contains information regarding the operation of the medical device, such as but not limited to, a flow rate, an occlusion setting, alarms and operating parameters.

Data streams pass through communication port 120g to bridge 142 via the cable communication path 140. Alternatively, as indicated previously and described in detail further herein, the data streams pass from antenna 120e to wireless transceiver 114, via wireless communication path 128.

In an embodiment, bridge 142 can have a plurality of ports 214. In bridge 142, the data stream interacts with the identifying data produced by the data stream identifier 204 and medical device identifier 206. Bridge 142 interfaces with cable communication system 110. The identified data streams then exits the bridge 142. The identified data streams can then interact with other data traffic in network 102.

The data stream identifier 204 can be incorporated into a Dallas Semiconductor DS 2505-UNW or the like. When a DS 2505-UNW is employed as the data stream identifier 204, the data stream identifier 204 can connect to pin 9 of a connector 210 such as the DB9 connector. The identifying data can be stored in memory elements, such as but not limited to, ROM elements, EEPROM memory elements, OTP EPROM memory elements, and NV SRAM memory elements. If the data stream identifier is connected to pin 9, the other 8 pins of the DB9 connector are free to pass the data stream from the serial port 120g to the cable communication path 140.

The medical device identifier 206 includes a programmable memory element that may be programmed to store data to identify the medical device. The stored data can include, but is not limited to, the information stored on the infusion pump ID 120d, the type of medical device, the baud rate, the service dates, and asset tags. Asset tags are inventory tags that uniquely identify the device they are associated with such as a serial number or other assigned identifier. Preferably, the memory element can be a one-time programmable memory element such as, but not limited to, an EEPROM memory element and an OTP EPROM memory element. The data stored on the memory element can be the data that the data stream identifier 204 attaches to the data streams in order to identify the data streams. In other embodiments, the data stored on the memory element can be provided upon an inquiry from the network 102. When a DS 2505-UNW and a DB9 connector are employed, the data stored on the memory element can be passed to the cable communication path 140 via pin 9 of the DB9.

The data stream identifier 204 and the medical device identifier 206 can be packaged in the same housing 208. For example, the DS2505-UNW from Dallas Semiconductor includes a data stream identifier 204 and a programmable EEPROM in the same housing. In one embodiment, the housing 208 is physically secured to the medical device so that if the medical device is disconnected from the cable communication path 140 or bridge 142 and moved to another part of the network 102, the network 102 will still recognize the data streams generated by the medical device as originating at the medical device.

Bridge 142 can include a plurality of serial ports 214 to communicate with a plurality of medical devices. The bridge 142 serial ports 214 include a pin for communication of the identifying data associated with the data streams. Bridge 142 merges the unidentified data stream from the medical device with the identifying data from the data stream identifier 204. The output of bridge 142 is the identified data stream. The unidentified data stream can enter bridge 142 through a plurality of serial port pins. For example, the unidentified data stream can enter bridge 142 on pins 1-8 of serial port 214 and the identifying data can enter bridge 142 on pin 9 of serial port 214. Bridge 142 can be a smart client bridge. Bridge 142 includes software to read the identifying data of the data stream. Bridge 142 can also be configured to only communicate with medical equipment that is associated with data stream identifiers 204.

In a wireless data stream identification system, bridge 142 may interface with a wireless network access point such as transceiver 114. If bridge 142 is configured to interface with a wireless network access point, then bridge 142 can be mounted on the medical device and operably connected to antenna 120e so that the medical device is portable throughout the patient care system 100. Bridge 142 can be a device, such as but not limited to, a Serial Client Bridge by Symbol Technologies, Inc., a CT WLAN Serial Client Bridge by CyberTEC GmbH, a Bluetooth device, a Wifi device, a combination or Bluetooth and Wifi, a Spectrum24® Serial Client Bridge, or the like.

The programming of the medical device identifier 206 with the attributes of any particular medical device can be accomplished using extendable markup language (XML) and UniqueWare. Using programming such as UniqueWare, the data stream identifier 204 and the medical device identifier 206 can be associated with the medical device by connecting the cabled communication path 140 to the connector 210. One pin of the connector 210 can then be used to communicate with the data stream identifier 204 and the medical device identifier 206. The information to be communicated to program the medical device identifier can be read using a bar code reader, such as bar code readers 108e and 104e and scanners 338 (FIG. 3), to read the bar code label of the medical equipment. Programming software, such as UniqueWare, will then download the medical device ID to the medical device identifier 206. This information can then be accessible to the data stream identifier 204. The UniqueWare can also create a table to associate a plurality of medical devices with a plurality of medical device identifiers.

Figure 3:
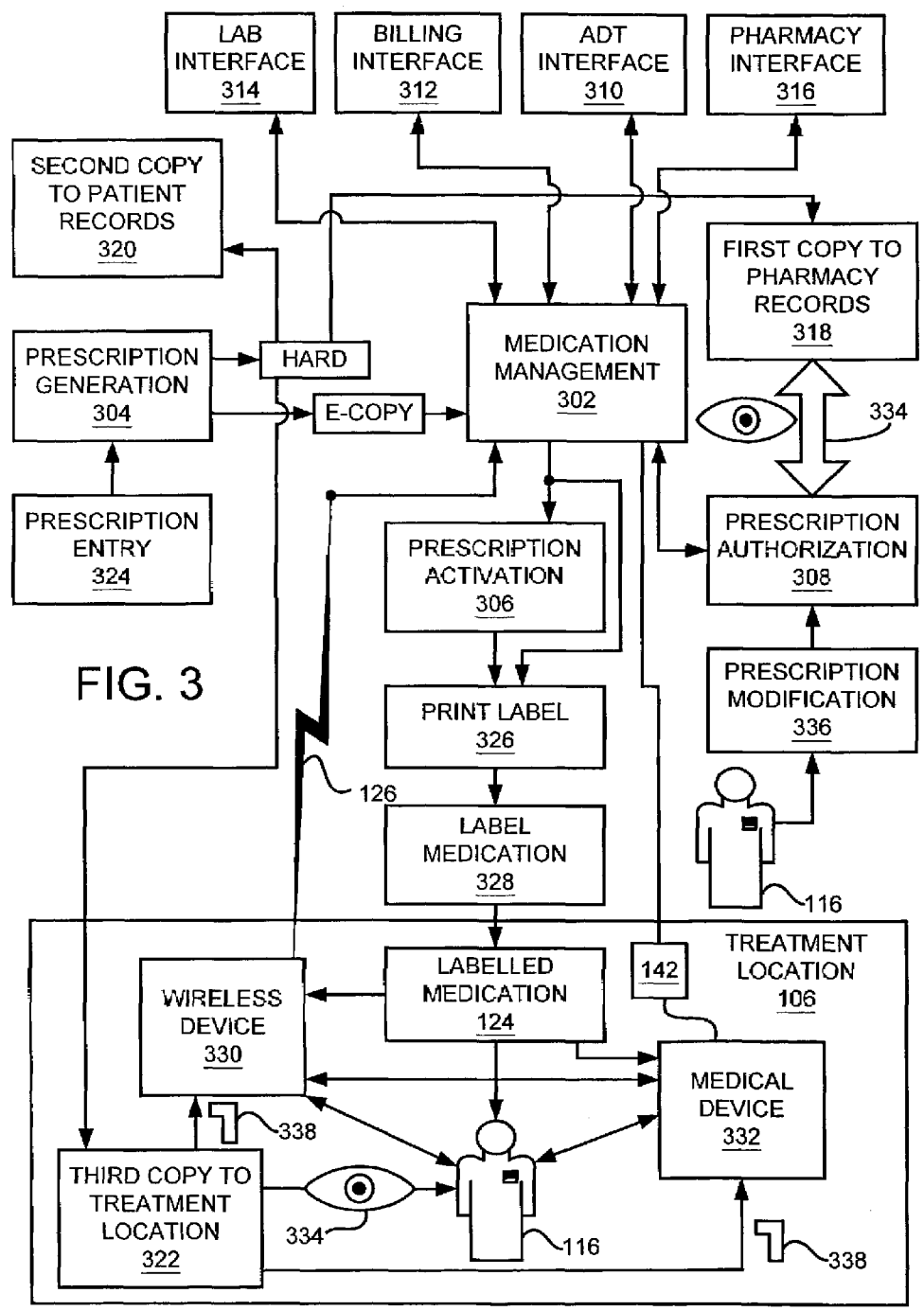
FIG. 3 is a block diagram showing functional components of the patient care system of FIG. 1.

FIG. 3 is a block diagram showing functional components of the patient care system 100 of FIG. 1. Some functional blocks of FIG. 3 include the ability to communicate using the current invention. For example, various functional blocks communicate with medical device 332 in FIG. 3. The system and method for uniquely identifying data streams associated with medical equipment can be practiced as a modular system where the modules represent various functions of the patient care system 100. FIG. 3 presents the system for uniquely identifying data streams associated with medical equipment as a system for identifying data streams. The flexibility of the system can be enhanced when the system is practiced as a modular system. The modules of the system can be included in various portions of the patient care system 100. The patient care system 100 includes a medication management module 302, a prescription generation module 304, a prescription activation module 306, and a prescription authorization module 308.

The medication management module 302 can coordinate the functions of the other modules in the patient care system 100 that are involved in the administration of medical treatment. The medication management module 302 will generally coordinate with other portions of the patient care system 100. The medication module 302 can include sub-modules for operating and/or interfacing with a CPOE, for operating and/or communicating with point-of-care modules, and for operating and/or communicating with medical treatment comparison modules. In FIG. 3, an admissions, discharge, and transfer (ADT) interface 310, a billing interface 312, a lab interface 314, and a pharmacy interface 316 are shown. ADT interface 310 can be used to capture information such as the patient's size, weight, and allergies. Pharmacy interface 3164 imports orders from the pharmacy. The pharmacy interface 316 can be an HL7 type of interface that interfaces with other systems for entering orders, such as a CPOE. This ability reduces the necessity for entering data into the patient care system 100 more than once. The pharmacy interface 316 can be configured to communicate with commercially available systems such as, but not limited to Cerner, HBOC, Meditech, SMS, and Phamous. Various other interfaces are also known to those having ordinary skill in the art but are not shown in FIG. 3 for clarity.

The medication management module 302 can have additional features such as the ability to check for adverse reactions due to drug-to-drug incompatibility, duplicate drug administration, drug allergies, drug dosage limitations, drug frequency limitations, drug duration limitations, and drug disease contraindications. Food and alcohol interactions can also be noted. Drug limitations can include limitations such as, but not limited to, limitations associated with adults, children, infants, newborns, premature births, geriatric adults, age groupings, weight groupings, height groupings, and body surface area. Generally, the medication management module 302 can prevent the entry of the same prescription for the same patient from two different sources within the patient care system 100.

The medication management module 302 can also include the ability to generate reports. The reports include, but are not limited to, end-of-shift, titration information, patient event lists, infusion history, pump performance history, pump location history, and pump maintenance history. The end-of-shift report can include the pump channel, start time, end time, primary infusion, piggyback infusion, medication, dose, rate, pump status, volume infused, volume remaining, time remaining, and the last time cleared. The infusion history report includes medications and volume infused.

The medication management module 302 can also include a medical equipment status database. The medical equipment status database includes data indicating the location of a medical device 332 within the patient care system 100. The medical equipment status database can also include data indicating the past performance of a medical device 332. The medical equipment status database can also include data indicating the maintenance schedule and/or history of a medical device 332.

The prescription generation module 304 generates hard prescriptions and electronic (E-copy) prescriptions. Hard prescriptions are generally produced in triplicate in medical facilities. A first hard copy 318 is generally sent to the pharmacy, a second hard copy 320 is generally kept for the patient's records, and third hard copy 322 is sent to treatment location 106. An electronic prescription is sent to the medication management module 302.

A computerized physician order entry (CPOE) system can be employed to carry out some or all of the functions of the prescription generation module 304. Clinicians 116 can enter data in a variety of manners such as, but not limited to, using a tablet wireless computer, medical treatment cart 132, and a workstation.

Prescription generation can include calculating the dose based on patient weight and/or height (from the ADT interface 310), the drug amount, diluent volume, concentration, and rate. Prescription generation 304 can include confirming operating parameters. The operating parameters can be based on information from a prescription entry module 324. Prescription generation may occur anywhere in the patient care system 100 such as, but not limited to, the pharmacy, the treatment location 106, and a nursing center.

Infusion prescriptions can include prescriptions such as, but not limited to, single dose infusions, intermittent infusions, continuous infusions, sequencing, titrating, and alternating types. Infusion prescriptions can also include total parenteral nutritional admixtures (TPN), chemotherapy continuous infusion, piggybacks, large volume parenterals, and other infusion prescriptions. The patient care system 100 is capable of functioning without end dates for orders. The patient care system 100 can use a continuous schedule generator that looks ahead a predefined time period and generates a schedule for admixture filling for the time period. The predefined time period can be defined at the patient care system 100 level or at subsystem levels such as the clinical discipline level and an organizational level. The predefined time periods can be adjustable by the clinician 116 entering the order. The schedule can be automatically extendable as long as the order is active in the patient care system 100.

The medication management module 302 can interface with more than one prescription generation module 304. The medication management module may receive orders from anywhere within the patient care system 100.

The pharmacy computer 104 is able to access the electronic copy from the medication management module 302. The prescription activation module 306 is a computer assisted system for coordinating the filling and labeling of prescriptions. The filling of the prescription and the creation or location of medication 124 from stock is handled by the prescription activation module 306.

While activating the prescription, the prescription activation module 306 can calculate the flow rate, if not specified in the prescription, the number of solutions/bags required for a specified period of time, the time period over which each solution/bag is to be administered, and the total volume of each solution/bag based on the concentration of the ingredients in the solution. Flow rates, volume to be infused, and/or duration may be adjusted in the system 100 wherein the system will automatically calculate dependent quantities, based on calculations, if the maximum dosage for the ingredients in the concentration would be exceeded as identified in the ingredient's medication file, the patient care system 100 will alert the pharmacist and/or clinician 116 and may ask for a reason code for the adjustment.

The patient care system 100 may bypass the prescription activation module 306. This may occur if the clinician, such as the patients' physician, has the authority to immediately activate an order. If the order is immediately activated, the medication management module may go directly to prescription labeling module 326.

In block 326, the patient care system 100 prints the medication label 124. The prescription can be printed remotely and will often be printed by the pharmacy printer 104*d*. After block 326, the patient care system goes to block 328. In block 328, the medication label 124*a* is attached to the medication 124. The pharmacist generally provides a visual verification 334 that the medication label 124*a* matches the first hard copy 318 of the prescription. FIG. 3 shows that a visual verification 334 is also associated with prescription authorization module 308. The medication 124 can then be transported from the pharmacy to the treatment location 106. A portable medical treatment cart 132 can be used for a portion of the route from the pharmacy to the treatment location 106.

The medication label 124*a* can include information for admixing. If not generated within patient care system 100, medication label 124*a* can be provided by a bulk medication supplier. If provided by a bulk medication supplier, the patient care system 100 has the capability of coordinating gathering the information from the medication label 124*a*. In addition, the patient care system 100 has the ability to add information, such as a patient identifier, to medication label 124*a*.

The medication labeling module 328 places the medication label 124 on the medication 124. This can be accomplished manually. This can also be accomplished using an automatic prescription filling and packaging system (not shown). If an automatic filling and packaging system is used, medication labeling module 328 provides data for coordination of the labeling of the medication 124 to the filling and packaging system.

At the treatment location 106, the clinician 116 uses a wireless device 330, such as digital assistant 118 and/or medical treatment cart 132, to verify and administer medication 124 to the patient 112. Wireless device 330 communicates with the medication management module 302 via a communication path, such as first communication path 126.

Clinician 116 generally identifies his/herself by scanning her badge 116*a*, identifies the patient 112 by scanning wristband 112*a*, identifies the medication 124 by scanning medication label 124*a*, and identifies the medical device 332, such as infusion pump 120, by scanning label 120*d*. The clinician 116 may also identify his/herself by providing a fingerprint and/or password. The medical device 332 may be a medical device capable of two-way communication with the medication management module 302. Alternatively, the medical device 332 may only be capable of providing information to the medication management module 302. Any communication from the medical device 332 will always be recognized as originating from the medical device 332 due to the data stream identification system. The data stream identification system assists the clinician 116 in administering and verifying the medical treatment. In one embodiment, the data stream identification system will generally result in the downloading of operating parameters to the medical device 332. The clinician 116 may generally provide a visual verification to confirm the third copy 322 and/or the MAR matches the labeled medication 124. Scanner 338 may be used to enter machine readable information from the third copy 322 to the wireless device 330 and the medical device 332.

The patient care system 100 includes the ability to make adjustments and modifications to infusion orders. Among other modules that can include the ability to make infusion adjustments are prescription entry 324, prescription activation 306, prescription authorization 308, and prescription modification module 336. Clinician 116 can access prescription modification module 336 in order to make adjustments to an order. The clinician 116 can access the prescription modification module 336 throughout the patient care system 100.

However, one very useful location for the clinician 116 to access the prescription modification module 336 is in the treatment location 106.

In the prescription authorization module 308, the patient care system 100 determines whether the clinician 116 has the authority to independently modify an infusion order. The clinician 116 can be recognized by the patient care system 100 as having the authority to independently modify certain portions of the order. If the clinician 116 does not have the authority to independently modify the order, a pharmacist or physician may be requested to approve the modification entered by the clinician 116.

FIG. 4 is a block diagram of a computer 400. Computer 400 may be the pharmacy computer 104, the central system 108, a CPOE, the digital assistant 118 of FIG. 1, and/or a computer included in any number of other subsystems that communicate via the network 102. Computer 400 includes an embodiment of the system for uniquely identifying data streams associated with medical equipment 410. In an embodiment, the system for identifying data streams 410 verifies that the right medication is provided to the right patient in the right dose at the right time, and via the right route. In another embodiment, the system for identifying data streams 410 provides a subset of these desirable verification features. In yet another embodiment, the programming of the infusion pump 120 can be based on operating parameters received from the pharmacy computer 104, and/or another remote computer. In a further embodiment, the programming of the infusion pump 120 can be based on operating parameters that are confirmed as correct by the pharmacy computer 104, another remote computer, and/or the clinician 116. The operating parameters and/or confirmations can be transported via the cable communication system 110 and the first and second wireless communication paths 126 and 128.

A critical concern in the art is that the right medication is administered to the right patient. Therefore, the system for identifying data streams 410 includes features to assist in assuring that the right medication is administered to the right patient in an efficient manner. The system for identifying data streams 410 of the invention can be implemented in software, firmware, hardware, or a combination thereof. In one mode, the system for identifying data streams 410 is implemented in software, as an executable program, and is executed by one or more special or general purpose digital computer(s), such as a personal computer (PC; IBM-compatible, Apple-compatible, or otherwise), personal digital assistant, workstation, minicomputer, or mainframe computer. An example of a general purpose computer that can implement the system for identifying data streams 410 of the present invention is shown in FIG. 4. The system for identifying data streams 410 can reside in, or have portions residing in, any computer such as, but not limited to, the pharmacy computer 104, the central system 108, and/or the digital assistant 118. Therefore, computer 400 of FIG. 4 may be representative of any computer in which the system for identifying data streams 410 resides or partially resides.

Generally, in terms of hardware architecture, as shown in FIG. 4, the computer 400 includes a processor 402, memory 404, and one or more input and/or output (I/O) devices 406 (or peripherals) that are communicatively coupled via a local interface 408. The local interface 408 can be, for example, but not limited to, one or more buses or other wired or wireless connections, as is known in the art. The local interface 408 can have additional elements, which are omitted for simplicity, such as controllers, buffers (caches), drivers, repeaters, and receivers, to enable communications. Further, the local interface can include address, control, and/or data connections to enable appropriate communications among the other computer components.

Processor 402 is a hardware device for executing software, particularly software stored in memory 404. Processor 402 can be any custom made or commercially available processor, a central processing unit (CPU), an auxiliary processor among several processors associated with the computer 400, a semiconductor based microprocessor (in the form of a microchip or chip set), a macroprocessor, or generally any device for executing software instructions. Examples of suitable commercially available microprocessors are as follows: a PA-RISC series microprocessor from Hewlett-Packard Company, an 80x86 or Pentium series microprocessor from Intel Corporation, a PowerPC microprocessor from IBM, a Sparc microprocessor from Sun Microsystems, Inc., or a 68xxx series microprocessor from Motorola Corporation. Processor 402 can also represent a distributed processing architecture such as, but not limited to, SQL, Smalltalk, APL, KLisp, Snobol, Developer 400, MUMPS/Magic.

Memory 404 can include any one or a combination of volatile memory elements (e.g., random access memory (RAM, such as DRAM, SRAM, SDRAM, etc.)) and nonvolatile memory elements (e.g., ROM, hard drive, tape, CDROM, etc.). Moreover, memory 404 can incorporate electronic, magnetic, optical, and/or other types of storage media. Memory 404 can have a distributed architecture where various components are situated remote from one another, but are still accessed by processor 402.

The software in memory 404 can include one or more separate programs. The separate programs comprise ordered listings of executable instructions for implementing logical functions. In the example of FIG. 4, the software in memory 404 includes the system for identifying data streams 410 in accordance with the present invention and a suitable operating system (O/S) 412. A non-exhaustive list of examples of suitable commercially available operating systems 412 is as follows: (a) a Windows operating system available from Microsoft Corporation; (b) a Netware operating system available from Novell, Inc.; (c) a Macintosh operating system available from Apple Computer, Inc.; (d) a UNIX operating system, which is available for purchase from many vendors, such as the Hewlett-Packard Company, Sun Microsystems, Inc., and AT&T Corporation; (e) a LINUX operating system, which is freeware that is readily available on the Internet; (f) a run time Vxworks operating system from WindRiver Systems, Inc.; or (g) an appliance-based operating system, such as that implemented in handheld computers or personal digital assistants (PDAs) (e.g., PalmOS available from Palm Computing, Inc., and Windows CE available from Microsoft Corporation). Operating system 412 essentially controls the execution of other computer programs, such as the system for identifying data streams 410, and provides scheduling, input-output control, file and data management, memory management, and communication control and related services.

The system for identifying data streams 410 can be a source program, executable program (object code), script, or any other entity comprising a set of instructions to be performed. When a source program, the program needs to be translated via a compiler, assembler, interpreter, or the like, which may or may not be included within the memory 404, so as to operate properly in connection with the O/S 412. Furthermore, the system for identifying data streams 410 can be written as (a) an object oriented programming language, which has classes of data and methods, or (b) a procedural programming language, which has routines, subroutines, and/or functions, for example but not limited to, C, C++, Pascal, Basic, Fortran, Cobol, Perl, Java, and Ada. In one embodiment, the system for identifying data streams 410 is written in C++. In other embodiments, the system for identifying data streams 410 is created using Power Builder. The I/O devices 406 may include input devices, for example but not limited to, a keyboard, mouse, scanner, microphone, touch screens, interfaces for various medical devices, bar code readers, stylus, laser readers, radio-frequency device readers, etc. Furthermore, the I/O devices 406 may also include output devices, for example but not limited to, a printer, bar code printers, displays, etc. Finally, the I/O devices 406 may further include devices that communicate both inputs and outputs, for instance but not limited to, a modulator/demodulator (modem; for accessing another device, system, or network), a radio frequency (RF) or other transceiver, a telephonic interface, a bridge, a router, etc.

If the computer 400 is a PC, workstation, PDA, or the like, the software in the memory 404 may further include a basic input output system (BIOS) (not shown in FIG. 4). The BIOS is a set of essential software routines that initialize and test hardware at startup, start the O/S 412, and support the transfer of data among the hardware devices. The BIOS is stored in ROM so that the BIOS can be executed when computer 400 is activated.

When computer 400 is in operation, processor 402 is configured to execute software stored within memory 404, to communicate data to and from memory 404, and to generally control operations of computer 400 pursuant to the software. The system for identifying data streams 410 and the O/S 412, in whole or in part, but typically the latter, are read by processor 402, perhaps buffered within the processor 402, and then executed.

When the system for identifying data streams 410 is implemented in software, as is shown in FIG. 4, it should be noted that the system for identifying data streams 410 can be stored on any computer readable medium for use by or in connection with any computer related system or method. In the context of this document, a computer readable medium is an electronic, magnetic, optical, or other physical device or means that can contain or store a computer program for use by or in connection with a computer related system or method. The system for identifying data streams 410 can be embodied in any computer-readable medium for use by or in connection with an instruction execution system, apparatus, or device, such as a computer-based system, processor-containing system, or other system that can fetch the instructions from the instruction execution system, apparatus, or device and execute the instructions. In the context of this document, a "computer-readable medium" can be any means that can store, communicate, propagate, or transport the program for use by or in connection with the instruction execution system, apparatus, or device. The computer readable medium can be for example, but not limited to, an electronic, magnetic, optical, electromagnetic, infrared, or semiconductor system, apparatus, device, or propagation medium. More specific examples (a non-exhaustive list) of the computer-readable medium would include the following: an electrical connection (electronic) having one or more wires, a portable computer diskette (magnetic), a random access memory (RAM) (electronic), a read-only memory (ROM) (electronic), an erasable programmable read-only memory (EPROM, EEPROM, or Flash memory) (electronic), an optical fiber (optical), and a portable compact disc read-only memory (CDROM) (optical). Note that the computer-readable medium could even be paper or another suitable medium upon which the program is printed, as the program can be electronically captured, via, for instance, optical scanning of the paper or other medium, then compiled, interpreted or otherwise processed in a suitable manner if necessary, and then stored in a computer memory.

In another embodiment, where the system for identifying data streams 410 is implemented in hardware, the system for identifying data streams 410 can be implemented with any, or a combination of, the following technologies, which are each well known in the art: a discrete logic circuit(s) having logic gates for implementing logic functions upon data signals, an application specific integrated circuit (ASIC) having appropriate combinational logic gates, a programmable gate array(s) (PGA), a field programmable gate array (FPGA), etc.

FIG. 5 is a flowchart showing an exemplar embodiment 500 of the system for identifying data streams 410 of FIG. 4. The system for identifying data streams 500 is called in block 502. In block 504, the system 500 accesses information related to the identity of the clinician 116. A first source 506, such as digital assistant 118 may provide information related to the identity of the clinician 116. Digital assistant 118 may acquire the information by reading the clinician's badge 116a with a bar code reader. First source 506 may also be another computer located at the remote location. First source 506 may be other sources of information such as, but not limited to, a bar code, such as a bar code included in clinician's badge 116a, a tag, laser readable data, radio-frequency readable data, a keyboard, an iButton reader, a fingerprint scanner, and a bar code reader that is not associated with digital assistant 118. Block 504 may include converting a signal generated by first source 506 to a computer readable medium format. Block 504 may also include using the information provided by first source 506 to match the information to the identity of the clinician 116 through the use of a look-up table stored in memory 404. After block 504, the system 500 goes to block 508.

In block 508, the system 500 identifies the patient 112. First source 506 may provide information related to the identity of the patient 112. Digital assistant 118 may acquire the information by reading the patient's wristband 112a with a bar code reader. Block 508 may include converting a signal generated by first source 506 to a computer readable medium format. Block 508 may also include using the information provided by first source 506 to match the information to the identity of the patient 112 through the use of a look-up table stored in memory 404 or any other matching process. After block 508, the system 500 goes to block 510.

In block 510, the system 500 identifies the treatment. The treatment may be the administration of medication 124. First source 506 may provide information related to the identity of the treatment. The identity of the treatment may include the identification of a medication 124. The medication identity may be correlated with a medication identifier. The medication identifier may include information such as, but not limited to, a medication identification number, a mixture identification number, a patient 112 encounter number, a drug name, a dosage, a manufacturer, a batch, an expiration date, and/or a drug prescriber. In block 510, any edubytes, messages, hazard warnings, and/or administrative instructions may be displayed on the digital assistant 118. Administrative instructions may include specialty set, filter requirements, warnings, and precautions. In block 510, if the medical treatment is a medication, the system 500 may check for expirations, such as the expiration of an admixture and lot recalls.

Digital assistant 118 may acquire information by reading medication label 124a with a bar code reader. Block 510 may include converting a signal generated by first source 506 to a computer readable medium format. Block 508 may also include using the information provided by first source 506 to match the information to the identity of the medical treatment through the use of a look-up table stored in memory 404 or other matching algorithms. After block 510, the system 500 goes to block 512.

In block 512, the system 500 determines whether the medical treatment has been previously associated with patient 112. The determination will often be made by the device that gathers data related to the identity of the patient and the medical treatment. For example, a clinician 116 may use the digital assistant 118 as the first source 506 to read a bar code from a patient's wristband 112a. The clinician 116 may then use the digital assistant 118 to read medication label 124a. The digital assistant 118 may then determine whether the patient identifier from the patient's wristband 112a is equivalent to the patient identifier from the medication label 124a.

One manner of previously associating the medical treatment with the patient is to associate the patient and the medical treatment in the central system 108 and/or in the pharmacy system 104. A physician may make the association through a computerized prescription ordering system. A pharmacist may make the association by entering a patient identifier and a medication identifier in the pharmacy system 104 where the medication identifier includes the patient identifier. The patient identifier may be derived from input sources such as, but not limited to, admission records, orders, an electronic physician order entry system, and/or prescriptions.

If the system 500 determines the medical treatment has not been previously associated with patient 112, the system 500 moves to block 516 where an alarm/error status is provided by the system 500. Block 516 may include displaying the alarm/error status on the digital assistant 118. If the system 500 determines the medical treatment has been previously associated with patient 112, the system 500 moves to block 514.

In block 514, the system 500 identifies the medical device. The medical device is configured to be the type that delivers the medical treatment to the patient. For example, the medical device may be infusion pump 120 if the medical treatment is medication 124. First source 506 may provide information related to the identity of the medical device. Digital assistant 118 may acquire the information by reading label 120d with a bar code reader. Block 514 may include converting a signal generated by first source 506 to a computer readable medium format. Block 514 may also include using the information provided by first source 506 to match the information to the identity of the medical device through the use of a look-up table stored in memory 404 or other matching algorithm. The information related to the identity of the medical device may also be stored in the medical device identifier 206.

Block 514 may include identifying sub-systems of the medical device. For example, if the medical device is an infusion pump, the infusion pump may have multiple channels. The channels may have barcodes. The channels may be associated with a primary medication and a "piggyback" medication. Block 514 may include identifying these sub-systems, including piggybacks. After block 514, the system 500 goes to block 518.

In block 516, the system 500 provides an alarm/error status signal. The alarm/status signal may be triggered by a variety of circumstances such as, but not limited to, the system 500 does not recognize the patient, the system 500 does not recognize the treatment, the system 500 cannot match the treatment to an order, the system 500 cannot identify the medical device 332, the operating parameters are not equivalent, and the treatment parameters are outside the treatment tolerances. The treatment tolerances may be defined at the patient care system 100 level or as a subset of the patient care system 100.

In block 518, the system for identifying data streams 500 determines whether the operating parameters are correct. The operating parameters are correct if they are consistent with a verified medical treatment. The system 500 may include the downloading of operating parameters to the medical device. The operating parameters may be downloaded from a variety of sources such as, but not limited to, pharmacy computer 104, medication label 124a, digital assistant 118, and the clinician 116 may manually enter the operating parameters. One check that may be performed is to confirm the dose is not outside of preset tolerances. The operating parameters may be parameters such as, but not limited to, a flow rate per unit of time, a quantity of medication, a dosing unit, a dosing duration, a dosing volume, a drug name, a dose unit, and a monitoring limit. The dosing information may be provided directly or based on patient 112 attributes such as patient weight.

If the operating parameters are not correct, the system 500 goes to block 516 and returns an error message. If the operating parameters are correct, the system for identifying data streams 500 may display the flow rate and dose information. The display may appear on display 120c, and/or digital assistant 118.

In block 520, the system 500 determines whether the treatment is correct. The treatment is correct if the treatment is for the patient, the treatment includes the right medication 124, the treatment includes the correct amount of medication, and the treatment is being administered at the right time. The clinician may also be queried to verify the right route by visually inspecting the medical device and related equipment. The clinician 116 may change some parameters, such as the timing of the medical treatment. If changed, a record of the change is generally kept in the patient care system 100. If the system 500 determines the treatment is not correct, the system 500 goes to block 516 and provides an error message. If the system 500 determines the treatment is correct, the system 500 goes to block 522.

Among the factors that may be considered in determining whether the treatment is correct, the system 500 may look to general rules, "look-alike" checks, and "sound-alike" checks. The general rules may include rules, such as but not limited to, a maximum flow rate that applies to all medications throughout the treatment facility, a maximum flow rate for the medication, and general rules based on patient characteristics, and a combination of these rules.

In block 522, the system 500 enables the medical device. This may include the clinician 116 providing a start signal to begin the infusion. In the event the medical device is in delayed start mode, block 520 may include providing a signal that the operating parameters have been downloaded and the medical device should provide the treatment as soon as the delay period is over. Block 522 may also include querying the medical device in order to confirm the correct medical device is being used to administer the correct medication to the correct patient. The query may include requesting that the medical device identifier 206 provide data to identify the medical device.

Downloading of operating parameters may include determining whether the patient identifier associated with the medical treatment and/or the patient identifier retrieved from the wristband 112a, is the same as the patient identifier associated with the medical treatment at the central location. The determination will often be made by the first computer, for example, the pharmacy computer 104a. If the system 500 determines the various patient identifiers are not the same the system may move to block 516. If the system 500 determines the various patient identifiers are the same, the system 500 may download the operating parameters directly to the medical device. The system 500 may send the operating parameters to a medical device such as infusion pump 120.

In block 524, the system 500 monitors the administration of the medical treatment. While the system 500 monitors the medical treatment administration, any changes to the operating parameters of the pump may be reflected throughout the patient care system 100 within 10 seconds. The changes may be noted on the digital assistant 118. During the infusion, the clinician 116 can adjust the infusion parameters. The adjustment may be to the flow rate of the infusion. Clinician 116 generally has the authority to adjust the flow rate within predefined boundaries. This allows the clinician 116 to "catch-up" if the infusion tubing is blocked or other interruptions occur.

Block 524 may also include accessing information related to the identity of a medical device. Accessing information related to the identity of the medical device may include generating a medical device tag using the medical device identifier 206. The medical device tag includes information to uniquely identify the medical device. Block 524 may also include accessing information using the data stream identifier 204 to generate a unique data tag and attaching the unique data tag to data streams generated by the medical device. The network 102 then processes data streams that include the unique data tag generated by the data stream identifier 204.

In block 526, the data stream identification system 500 records the result of the medical treatment administration. The result may be the successful administration of the medical treatment pursuant to the operating parameters. However, other results are possible such as, but not limited to, a patient's refusal to accept the medical treatment, a modification of the medical treatment, and equipment malfunction, and an interstitial infusion error. In the case of a modification of the medical treatment, a modified order may be generated. The modified order may then be linked in the medication management module 302 with the original order.

Various blocks of the system for identifying data streams 500, such as blocks 518 to 524, may include displaying treatment information on the digital assistant 118. This may include displaying information that mirrors the information on display 120c of infusion pump 120. The information on display 120c may be supplemented with information about the patient, the patient location, and the infusion order. This information may include information regarding multiple channels of infusion pump 120. The displayed information may include information such as, but not limited to, personality, prompt line, status line, operating icons and pump head display. Operating icons include falling drop, stop sign, flow check piggyback, Guardian, and delay start. The pump head display includes information such as the drug label and the infusion rate. Those having ordinary skill in the art are familiar with the displayed information and operating icons described above.

In another embodiment, the system for identifying data streams 500 may determine there is no information stored in the patient care system 100 related to the medical treatment the clinician 116 desires to administer to the patient 112. If the patient care system 100 recognizes the clinician 116 as having the authority to initiate the desired medical treatment, the system 500 may allow for the administration of the medical treatment without going to block 516.

Throughout this document and the related claims, "central location" and "remote location" are relative terms to each other. A "remote location" is any location where a patient is receiving treatment through a controlled medical device, such as a patient treatment location 106 where patient 112 is receiving treatment through an infusion pump 120. A "central location" is any location, other than the remote location, where parameters for operating the medical device are accessible such as, but not limited to, the location of the pharmacy computer 104 and the central system 108. In a typical arrangement, several remote locations, such as treatment location 106, are in communication with a central location.

One benefit of the system for identifying data streams 500 is that the operating parameters for the medical device do not have to pass through digital assistant 118, or any other computer in the remote location prior to the operating parameters being available to program the medical device. Bypassing computers at the remote location eliminates a potential source of errors in administering medication 124 to a patient 112. The operating parameters for the medical device may be sent "directly" to the medical device assuming the various verifications are achieved. In this context, "directly" meaning that the operating parameters may be sent to the medical device without passing through the digital assistant, or any other computer in the remote location.

In another embodiment, the system 500 may include an additional block (not shown) where the central computer accepts a second medication identifier. The second medication identifier may be entered by the clinician 116 at the remote location. The second medication identifier may be a revised first medication identifier. For example, the second medication identifier may be part of the prescription or electronic physician order entry that is the source for the first patient ID and the operating parameters. The system 500 may then confirm the first and second medication IDs are equivalent prior to sending the operating parameters to the medical device. The second medication ID may be replaced by a revised first medication ID between the time the prescription is entered and the time the medication 124 arrives at the treatment location 106. The system 500 will then sound an alarm if second medication identifier is not equivalent to the first medication identifier that was included in the medication label 124a. In a further embodiment, the system 500 may include an additional block (not shown) where the operating parameter is used to program the medical device.

In one implementation of system 500, an order is entered in pharmacy computer 104. The order includes a first patient identifier and an operating parameter. The pharmacy computer 104 generates a medication label 124a that is affixed to medication 124. The medication 124 is sent to a treatment location 106. At treatment location 106, clinician 116 reads the clinician's badge 116a, patient's wristband 112a, and medication label 124a with a digital assistant 118. The digital assistant 118 determines whether medication label 124a and wristband 112a identify the same patient 112. The system 500 then sends the medication identifier to the pharmacy computer 104. The pharmacy computer 104 confirms the medication label 124a identifies the same patient as the order and sends the operating parameter to an infusion pump. The operating parameter may be sent directly to the infusion pump. The operating parameter is then used to program the infusion pump to administer the medication 124 to the patient 112. The system 500 enables the pump and then monitors the treatment. While monitoring the treatment, the communication from the pump includes accessing information related to the identity of the medical device and processing data streams from the pump that are identified by a unique data tag. Accessing information related to the identity of the medical device includes generating a unique medical device tag. Accessing information related to the identity of the medical device also includes generating a unique data tag using a data stream identifier 204 and attaching the unique data tag to data streams generated by the medical device.

Any process descriptions or blocks in figures, such as FIG. 3 and FIG. 5, should be understood as representing modules, segments, or portions of code which include one or more executable instructions for implementing specific logical functions or steps in the process, and alternate implementations are included within the scope of the embodiments of the present invention in which functions may be executed out of order from that shown or discussed, including substantially concurrently or in reverse order, depending on the functionality involved, as would be understood by those having ordinary skill in the art.

It should be emphasized that the above-described embodiments of the present invention, particularly, any "preferred" embodiments, are merely possible examples of implementations, merely setting forth for a clear understanding of the principles of the invention. Many variations and modifications may be made to the above-described embodiment(s) of the invention without substantially departing from the spirit and principles of the invention. All such modifications are included within the scope of this disclosure and the present invention and protected by the following claims.

What is claimed is:

1. A system for identifying data streams, comprising:
    a medical device generating data streams, the data streams being transmissions of data from the medical device, the data streams including information regarding the operation of the medical device;
    a data stream identifier secured to the medical device and configured to generate a unique data tag that uniquely identifies data streams transmitted from the medical device;
    a medical device identifier secured to the medical device and including a programmable memory element configured to generate a medical device tag upon receipt of a request from an external computer, the medical device tag including information to uniquely identify the medical device; and
    a bridge configured to attach the unique data tag to the data stream, the bridge configured to provide the medical device tag to the external computer.

2. The system of claim 1, wherein the medical device is an infusion pump.

3. The method of claim 1 wherein the medical device is an oxygen monitor.

4. The system of claim 1, wherein the data streams include data regarding the operation of an infusion pump.

5. The system of claim 1, wherein the data streams include data regarding the status of a patient.

6. The system of claim 1, wherein the unique data tag is randomly generated after the data stream identifier is secured to the medical device.

7. The system of claim 1, wherein the medical device tag includes the medical equipment identifier.

8. The system of claim 1, wherein the external computer is at a central location.

9. The system of claim 1, wherein the bridge includes a plurality of ports.

10. A method for identifying data streams, comprising:
    providing for generating data streams with a medical device, the data streams being transmissions of data from the medical device, the data streams including information regarding the operation of the medical device;
    providing for generating a unique data tag that uniquely identifies data streams transmitted from the medical device using a data stream identifier secured to the medical device;
    providing for attaching the unique data tag to the data streams; and,
    providing for generating, upon request from an external computer, a medical device tag using a medical device identifier secured to the medical device and including a programmable memory element, the medical device tag including information to uniquely identify the medical device.

11. The method of claim 10, wherein the medical device is an infusion pump.

12. The method of claim 10, wherein the medical device is a ventilator.

13. The method of claim 10, wherein the medical device is a monitor of patient status.

14. The method of claim 13, wherein the monitor is an oxygen monitor.

15. The method of claim 10, wherein the data streams include data regarding the operation of an infusion pump.

16. The method of claim 10, wherein the data streams include data regarding the status of a patient.

17. The method of claim 10, wherein the unique data tag is randomly generated after the data stream identifier is secured to the medical device.

18. The method of claim 10, wherein the medical device tag includes the medical equipment identifier.

19. The method of claim 10, wherein the external computer is at a central location.

20. The method of claim 10, wherein the plurality of data streams are transmitted in a network using Bluetooth technology.

21. A method for identifying data streams, the method comprising the steps of:
    providing for accessing information related to the identity of a patient;
    providing for accessing information regarding the identity of a medical treatment, the medical treatment having a treatment type;
    providing for determining whether the medical treatment has been previously associated with the patient;
    providing for providing a first error signal if the medical treatment has not been previously identified with the patient;
    providing for generating a medical device tag to identify a medical device, the medical device configured to administer the medical treatment type, the medical device tag including information to uniquely identify the medical device, the medical device generating a plurality of data streams, the data streams including information regarding the operation of the medical device;
    providing for generating a unique data tag using a data stream identifier;
    providing for attaching the unique data tag to the data streams generated by the medical device;
    providing for determining whether a plurality of operating parameters for the medical device are consistent with the medical treatment, the operating parameters having been provided from a central computer, the operating parameters having been provided to the medical device without passing through a remote computer;
    providing for providing a second error signal if the operating parameters for the medical device are not consistent with the medical treatment;
    providing for enabling the medical device to provide the medical treatment to the patient; and,
    providing for verifying that the medical device is providing the medical treatment to the patient.

22. The method of claim 21, wherein the medical device is an infusion pump.

23. The method of claim 21 wherein the medical device is an oxygen monitor.

24. The method of claim 21, wherein the data streams include data regarding the operation of an infusion pump.

25. The method of claim 21, wherein the data streams include data regarding the status of a patient.

26. The method of claim 21, wherein the unique data tag is randomly generated after the data stream identifier is secured to the medical device.

27. The method of claim 21, wherein the medical device tag includes the medical equipment identifier.

28. The method of claim 21, wherein the central computer is at a central location.

29. The method of claim 21, wherein the data streams are transmitted in a network using Bluetooth technology.

30. The method of claim 21, wherein the central computer determines whether a plurality of operating parameters for the medical device are consistent with the medical treatment.

31. The method of claim 21, wherein accessing information related to the identity of a patient includes creating a digital photograph of the patient to compare to a stored digital photograph of the patient.

32. The method of claim 21, wherein the medical treatment includes the use of anesthesiology supplies.

33. The method of claim 21, wherein the medical treatment includes the administration of a medication and the medication container includes a machine readable label.

34. The method of claim 21, wherein the central computer determines inventory reorder set points for supplies used for the medical treatment.

35. At least one computer program for identifying data streams, the at least one computer program including logic for:
   accessing information related to the identity of a patient;
   accessing information regarding the identity of a medical treatment, the medical treatment having a treatment type;
   determining whether the medical treatment has been previously associated with the patient;
   providing a first error signal if the medical treatment has not been previously identified with the patient;
   generating a medical device tag to identify a medical device, the medical device configured to administer the medical treatment type, the medical device tag including information to uniquely identify the medical device, the medical device generating a plurality of data streams, the data streams including information regarding the operation of the medical device;
   generating a unique data tag using a data stream identifier;
   attaching the unique data tag to the data streams generated by the medical device;
   determining whether a plurality of operating parameters for the medical device are consistent with the medical treatment, the operating parameters having been provided from a central computer, the operating parameters having been provided to the medical device without passing through a remote computer;
   providing a second error signal if the operating parameters for the medical device are not consistent with the medical treatment;
   enabling the medical device to provide the medical treatment to the patient; and
   verifying that the medical device is providing the medical treatment to the patient.

36. The at least one computer program of claim 35, wherein the medical device is an infusion pump.

37. The method of claim 35 wherein the medical device is an oxygen monitor.

38. The at least one computer program of claim 35, wherein the data streams include data regarding the operation of an infusion pump.

39. The at least one computer program of claim 35, wherein the data streams include data regarding the status of a patient.

40. The at least one computer program of claim 35, wherein the unique data tag is randomly generated after the data stream identifier is secured to the medical device.

41. The at least one computer program of claim 35, wherein the medical device tag includes the medical equipment identifier.

42. The at least one computer program of claim 35, wherein the central computer is at a central location.

43. The at least one computer program of claim 35, wherein the data streams are transmitted in a network using Bluetooth technology.

44. The at least one computer program of claim 35, wherein the central computer determines whether a plurality of operating parameters for the medical device are consistent with the medical treatment.

45. The at least one computer program of claim 35, wherein accessing information related to the identity of a patient includes creating a digital photograph of the patient to compare to a stored digital photograph of the patient.

46. The at least one computer program of claim 35, wherein the medical treatment includes the use of anesthesiology supplies.

47. The at least one computer program of claim 35, wherein the medical treatment includes the administration of a medication and the medication container includes a machine readable label.

48. The at least one computer program of claim 35, wherein the central computer determines inventory reorder set points for supplies used for the medical treatment.

49. An apparatus comprising:
   a medical device having a data output comprising medical treatment information;
   a wireless device coupled to the data output and having a radio frequency (RF) output;
   a medical device tag associated with the medical device that is generated by a medical device identifier secured to the medical device and including a programmable memory element, the medical device tag comprising information to uniquely identify the medical device, the information provided upon request by an electronic device;
   a data stream identifier secured to the medical device and configured to generate an identifier output that is attached to the medical treatment information.

50. The apparatus of claim 49, wherein the medical device is an infusion pump.

51. The apparatus of claim 50, the medical treatment information comprising a fluid flow rate.

52. The apparatus of claim 51, wherein the medical device was originally manufactured without a wireless device.

* * * * *